United States Patent [19]

Watson et al.

[11] Patent Number: 5,728,071
[45] Date of Patent: Mar. 17, 1998

[54] INJECTION PATCH

[76] Inventors: Robert L. Watson, 1704 Singletree Way, Bowling Green, Ky. 42103; William R. Knepshield, 889 S. Matlack St., West Chester, Pa. 19382

[21] Appl. No.: 708,833

[22] Filed: Sep. 9, 1996

[51] Int. Cl.⁶ .............................. A61M 5/32; A61F 13/00
[52] U.S. Cl. ..................... 604/180; 604/174; 602/46; 602/48; 128/888
[58] Field of Search ............................. 604/174, 180, 604/304, 305, 307

[56] References Cited

U.S. PATENT DOCUMENTS

| | | | |
|---|---|---|---|
| 4,988,341 | 1/1991 | Columbus et al. | 604/304 X |
| 5,015,228 | 5/1991 | Columbus et al. | 604/304 X |
| 5,092,323 | 3/1992 | Riedel et al. | 604/305 X |
| 5,409,466 | 4/1995 | Watson et al. | 604/180 X |
| 5,447,492 | 9/1995 | Cartmell et al. | 604/180 X |
| 5,496,264 | 3/1996 | Watson et al. | 604/180 X |
| 5,569,207 | 10/1996 | Gisselberg et al. | 604/180 X |

*Primary Examiner*—Sam Rimell
*Assistant Examiner*—Robert V. Racunas
*Attorney, Agent, or Firm*—Walter C. Farley

[57] ABSTRACT

An injection patch for facilitating injection into a patient and for confining blood from the injection wound has an absorbent pad against the skin of a patient around an intended injection site and a second surface. An elastomeric, self-sealing membrane through which an injection needle can penetrate lies against the second surface of the pad and closes the central opening. A cover layer with a central opening overlies the membrane and exposing a central portion of it to identify the injection site. The patch is adhesively held to the patient's skin. An injection can be made with a needle passed through the membrane and the patient's skin, after which the needle is extracted while the membrane wipes the needle, reseals and forms a cavity with the pad and the patient's skin to contain blood from the injection site until after hemostasis.

4 Claims, 1 Drawing Sheet

INJECTION PATCH

FIELD OF THE INVENTION

This invention relates to an adhesive patch through which injections can be made for minimizing contact with the blood of a patient being injected.

BACKGROUND OF THE INVENTION

In recent years, it has been officially and widely recognized that blood-borne pathogens are an important and serious method of transmission of infectious diseases. health care workers in particular are in danger from such exposure, but the danger exists for any person who is likely to come in contact with the blood of a person who is infected with such a disease.

Commonly, when an injection is being made, the target area of the patient's skin is wiped with a disinfectant and the injection is made through the skin subcutaneously or intramuscularly using a needle and syringe. After the injection has been made, the needle is withdrawn and a pad of gauze or cotton is placed on the puncture wound to absorb any blood which may emanate therefrom. The pad may or may not be left in place or temporarily taped to the wound. Clearly, not only is the health care worker giving the injection in danger of exposure but so also is any other health care worker or other person who might come in contact with the area of the puncture wound.

The Occupational Safety and Health Administration (OSHA) and Center for Disease Control (CDC) have recommended that all human blood and other potentially infectious materials be treated as if known to be infectious for HIV, HBV or other blood-borne pathogens regardless of the perceived low risk of a patient or patient population. However, no effective means for meeting this recommended standard has existed.

SUMMARY OF THE INVENTION

An object of the present invention is to provide a patch through which an injection can be made and which contains blood under a sterile, self-sealing, non-coring, non-latex elastomeric membrane after an intramuscular or sub-cutaneous injection.

Another object is to provide such a patch which includes an adhesive absorptive circumferential pad for absorbing any blood coming in contact with it and containing the blood under the membrane.

Briefly described, the invention comprises an injection patch for facilitating injection into a patient and for confining blood from the injection wound including a generally annular absorbent pad having a first surface to be placed against the skin of a patient around an intended injection site, a second surface opposite said first surface and a central opening. An elastomeric, self-sealing membrane through which an injection needle can penetrate lies against the second surface of the pad and closes its central opening. A cover layer has a central opening substantially aligned with the central opening of the pad to expose a central portion of the membrane to identify the injection site, the cover layer being adhered to the membrane and the pad. The patch is adhesively held on the patient's skin, whereby an injection can be made with a needle passed through said membrane and the patient's skin. After the injection, the membrane wipes the needle and forms a cavity with the pad and the patient's skin to contain blood from the injection site until after hemostasis.

BRIEF DESCRIPTION OF THE DRAWINGS

In order to impart full understanding of the manner in which these and other objects are attained in accordance with the invention, particularly advantageous embodiments thereof will be described with reference to the following drawings, which form a part of this disclosure, and wherein.

DESCRIPTION OF THE PREFERRED EMBODIMENTS

Figure 1:
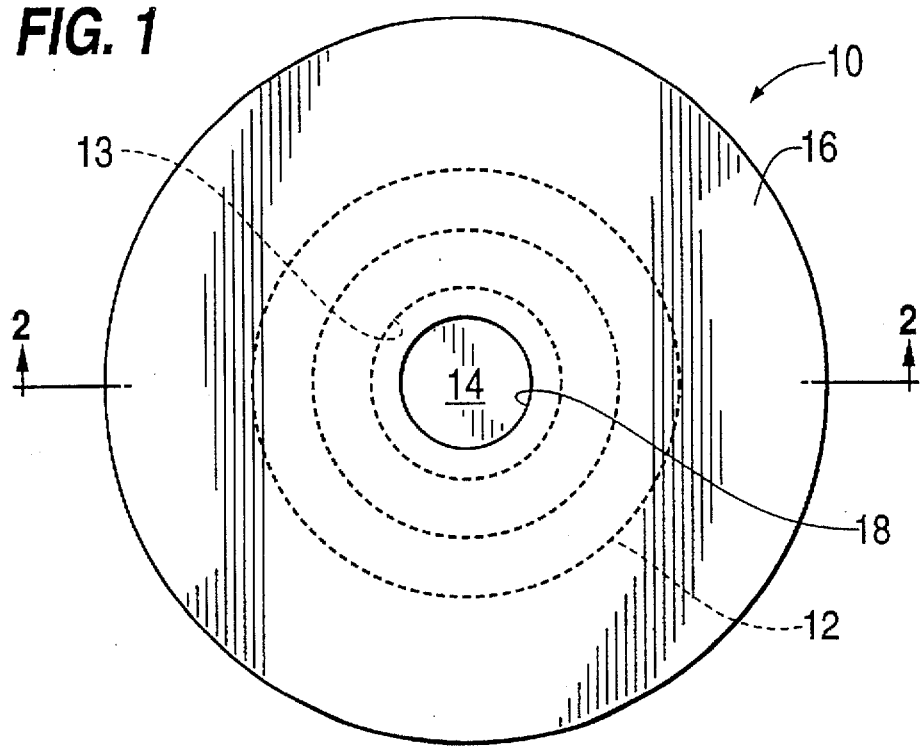
FIG. 1 is a top plan view of a patch in accordance with the invention.
Figure 2:
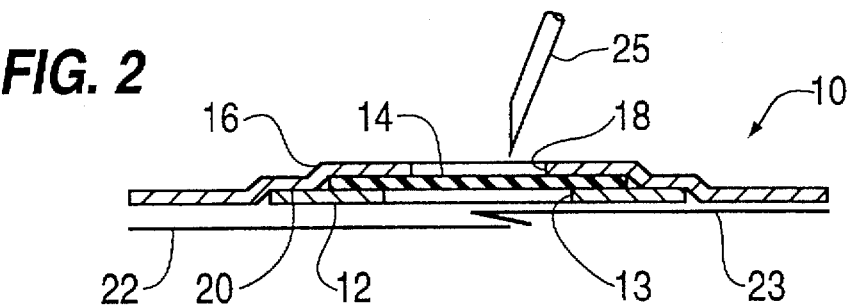
FIG. 2 is a side elevation, in section along line 2—2 of FIG. 1.

FIGS. 1 and 2 show an injection patch 10 in accordance with the invention which, in the embodiment shown, comprises an annular ring 12 of absorbent material with a central opening 13, a circular membrane 14 of self-sealing elastomeric material and a retaining or cover layer 16 having a central opening 18. Membrane 14 is smaller in diameter than the outer diameter of ring 12 and larger in diameter than opening 13.

The dimensions of the thicknesses of the various materials are exaggerated in the drawings for clarity. In a manufactured sample of the patch, the entire thickness of the thickest part of patch 10 is about $1/32$ to $1/16$ inch.

Figure 3:
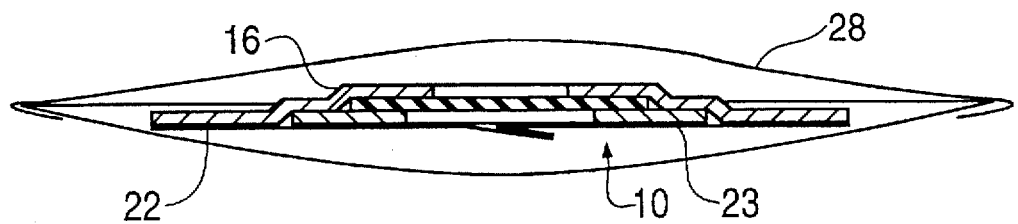
FIG. 3 is a sectional side elevation, similar to FIG. 2, of a patch in accordance with the invention as provided in a sterile package.

Retaining layer 16 has an outer surface which faces away from the membrane and absorbent material layers, and an inner surface 20 which is coated with an adhesive material. The adhesive material adheres layer 16 to the membrane and to the absorbent material and the peripheral area of layer 16 is available to hold the patch to the skin of a patient. Before use, this peripheral area and the absorbent material are covered with a conventional butterfly of release paper or plastic sheets, schematically indicated at 22 and 23, which are easily removable to expose the adhesive. As schematically shown in FIG. 3, a patch in accordance with the invention is supplied in a sealed paper or plastic package 28 having a sterile interior.

In use, the region of the skin where the injection is to be made, whether intramuscular or sub-cutaneous, is wiped with alcohol or the like. The patch is removed from its sterile package 28 and the release material butterflies 22 and 23 are removed to expose the adhesive surface of the peripheral area of layer 16. The patch is then applied to the skin where it is securely but removably held by the adhesive.

A conventional needle 25, connected to a syringe containing the substance to be injected, is then passed through the central hole in layer 16, through the central part of membrane 14 and into the skin. The angle of penetration of the needle can be freely selected by the health care worker depending on the type of injection being given. The substance in the syringe is then injected and the needle is extracted and disposed of in a manner consistent with safety regulations and practices.

As the needle is extracted, membrane 14 wipes from the needle any blood or other body fluids from the patient and the hole made by the needle automatically redoses, trapping blood from the puncture wound beneath the membrane. A closed cavity is created within which the blood is retained, this cavity being formed by the skin of the patient, the inner (skin-facing) surface of membrane 14 and the inwardly facing surfaces of hole 13 in pad 12. The patch is allowed to remain in place for an interval sufficient to allow hemostasis, typically about 20 minutes, and can then be removed by the patient in most cases.

Although the patch has been described with all of its parts being circular or annular, it will be recognized that layer 16 can easily have a rectangular or other polygonal shape and that the other components of the patch can also be varied as to shape and size. In a manufactured version of the embodiment shown, the outer diameter of the patch (layer 16) is about 1-7/8 inches with a central hole of 11/32 inch diameter. Membrane 14 has a diameter of 13/16 inch and pad 12 has a diameter of 1-1/8 inches with a central hole 13 which is 1/2 inch in diameter.

The described embodiment is believed to be the most effective and simplest to produce embodiment of the invention. However, it will be recognized that variations can be made in the relative sizes of the components and the choice of which component carries the means for holding the patch onto the patient's skin. For example, in the embodiment described, this means is a coating of adhesive on the periphery of layer 16 which is larger in diameter that the other components, providing a peripheral adhering portion. However, it is possible to make the diameter of the pad substantially equal to that of the cover layer and place the adhesive on the pad. The cover layer then performs the function of holding the components together and, by its central hole, identifying the injection site and does not touch the patient's skin at all.

While certain advantageous embodiments have been chosen to illustrate the invention, it will be understood by those skilled in the art that various modifications can be made therein without departing from the scope of the invention as defined in the appended claims.

What is claimed is:

1. An injection patch for facilitating injection into a patient and for confining blood from the injection wound comprising a generally annular absorbent pad having a first surface to be placed against the skin of a patient around an intended injection site, a second surface opposite said first surface and a central opening;

an elastomeric, self-sealing membrane through which an injection needle can penetrate, said membrane lying against said second surface and closing said central opening, said membrane, in use, being spaced from the patient's skin and forming a cavity between said membrane and said skin surrounded by said absorbent pad;

a cover layer having a central opening substantially aligned with said central opening of said pad and exposing a central portion of said membrane to identify the injection site; and means for adhesively holding said patch on the patient's skin, whereby an injection can be made with a needle passed through said membrane and the patient's skin, after which injection said membrane wipes said needle as said needle is withdrawn and said cavity between said pad and the patient's skin contains blood from the injection site until after hemostasis.

2. A patch according to claim 1 wherein said cover layer is generally circular and has a larger diameter than said pad.

3. A patch according to claim 2 wherein said membrane is generally circular and has a larger diameter than said central opening of said cover layer and a smaller diameter than said pad.

4. A patch according to claim 3 wherein said membrane and said pad are adhesively attached to said cover layer.

* * * * *